United States Patent [19] [11] 4,221,813
Breault et al. [45] Sep. 9, 1980

[54] TREATMENT OF HYPERTENSION

[75] Inventors: George O. Breault, Creamery; King C. Kwan, Doylestown, both of Pa.

[73] Assignee: Merck & Co., Inc., Rahway, N.J.

[21] Appl. No.: 945,355

[22] Filed: Sep. 25, 1978

Related U.S. Application Data

[63] Continuation of Ser. No. 782,146, Mar. 28, 1977, abandoned.

[51] Int. Cl.$^2$ .............................................. A61K 31/24
[52] U.S. Cl. ................................................... 424/309
[58] Field of Search ........................................ 424/309

[56] References Cited

U.S. PATENT DOCUMENTS 3,230,143  1/1966  Marcus .................................. 424/175

*Primary Examiner*—Stanley J. Friedman
*Attorney, Agent, or Firm*—Daniel T. Szura

[57] ABSTRACT

A method of treating hypertension by oral administration of the ethyl ester of L-α-methyl-3,4-dihydroxyphenylalanine or a pharmaceutically acceptable salt thereof, and pharmaceutical compositions are disclosed.

13 Claims, No Drawings

TREATMENT OF HYPERTENSION

This is a continuation application Ser. No. 782,146, filed, Mar. 28, 1977 now abandoned.

BACKGROUND OF THE INVENTION

The present invention involves a novel method of treating hypertensive patients. This method involves oral administration in a single dose of 500 mg. or more of ethyl[2-methyl-3(3,4-dihydroxyphenyl)]alaninate.

L-α-methyl-3,4-dihydroxyphenylalanine, also referred to as L-α-methyldopa, is a drug which is effectively used in treating hypertensive humans. The total effective daily dosage of L-α-methyldopa generally ranges from about 125 mg. to about 3,000 mg. per day, usually in divided doses.

The ethyl ester of L-α-methyldopa is known to be useful for intravenous administration to hypertensive patients in emergency situations (U.S. Pat. No. 3,230,143 issued Jan. 18, 1966).

For hypertensive patients who require a total daily dosage of 500 mg. or more of L-α-methyldopa for effective treatment, an improved antihypertensive effect is obtained when the corresponding amount of the ethyl ester of L-α-methyldopa is administered orally in a single dose daily. Said improvement in antihypertensive effect increases as the patient's daily requirement of L-α-methyldopa increases. Thus, e.g. among patients whose daily dosage requirements of L-α-methyldopa is 1,000 mg. or more, the same antihypertensive effect can be achieved with a smaller equivalent dose of the ethyl ester of L-α-methyldopa administered orally as a single dose daily.

SUMMARY OF THE INVENTION

A method of treating hypertension which comprises oral administration in single daily doses to a hypertensive human of 500 mg. or more of the ethyl ester of L-α-methyl-3,4-dihydroxyphenylalanine, or a pharmaceutically acceptable salt thereof. A pharmaceutical composition in unit dosage form suitable for use in the aforementioned treatment.

DESCRIPTION OF THE INVENTION

An embodiment of the present invention is a method of treating hypertension which comprises oral administration in a single dose to a hypertensive human of 500 mg. or more of the ethyl ester of L-α-methyl-3,4-dihydroxyphenylalanine, or a pharmaceutically acceptable salt thereof.

It is preferred that said dose is about 750 mg. to about 3000 mg., or more preferably 1000 mg.; 1500 mg. or 2000 mg. Single dose includes multiple dosage units. Treatment with a unit dosage form containing 750 mg. or more of said alanine or salt thereof is more preferred.

Pharmaceutically acceptable salts include salts of ethyl [L-α-methyl-3,4-dihydroxyphenyl]alaninate, also referred to herein as the ethyl ester of L-α-methyldopa, with suitable organic or inorganic acids. Suitable organic acids include carboxylic and non-carboxylic acids. Useful mono- or dicarboxylic acids are exemplified by acetic acid, malic acid, succinic acid, tartaric acid, oxalic acid, pamoic acid, 2,2-dimethylpropionic acid (pivalic acid), fumaric acid and the like. A useful non-carboxylic acid is isethionic acid. Useful inorganic acids include the hydrogen halides e.g. HCl, HBr, HI, sulfuric acid and phosphoric acid. The hydrochlorides are preferred salts.

Another embodiment of the present invention is a pharmaceutical composition for oral administration to hypertensive humans comprising more than 500 mg. of the ethyl ester of L-α-methyldopa, or a salt thereof, in combination with pharmaceutically acceptable compounding ingredients. Pharmaceutical compositions in unit dosage form containing about 750 mg. to about 1500 mg. of the ethyl ester or salt thereof are preferred. Compositions containing 750 mg or 1000 mg. of said ester or salt thereof are more preferred.

The pharmaceutical compositions are prepared using conventional procedures and compounding ingredients. While liquid formulations containing the required amount of alanine ester or salt thereof, may be prepared, the preferred oral administration form is non-sustained release.

The preferred dosage forms are exemplified by tablets, capsules, troches, powders, solutions, elixirs, syrups and the like. Conventional compounding ingredients, i.e. diluents, excipients, etc., are utilized in the pharmaceutical compositions. Examples of some common compounding ingredients are starch, calcium stearate, talc, flavor additives, vegetable gum, mineral oil, sesame oil, coloring additives, silica, lactose, glycerine, hydroalcoholic solutions and antioxidants. Representative pharmaceutical formulations are presented below:

| Tablet Formulation | |
|---|---|
| Methyldopate HCl | 978.9 mg. |
| Corn Starch | 134.7 mg. |
| Magnesium Stearate | 9.9 mg. |
| Soft Gelatin | |
| Capsule Formulation | |
| Methyldopate | 566.4 mg. |
| Butylated Hydroxytoluene | 0.001 mg. |
| Butylated Hydroxyanisole | 0.001 mg. |
| Sesame Oil | q.s. |
| Liquid Formulation | |
| Methyldopate HCl | 1305.2 mg. |
| Methylparaben | 6.0 mg. |
| Propylparaben | 1.0 mg. |
| Sodium Bisulfite | 10.0 mg. |
| Sorbitol Solution 50% q.s. ad. | 5.0 ml. |

The ethyl ester of L-methyldopa is also referred to herein as methyldopate.

In in-vivo (man) experiments, it was demonstrated that (1) the absorption of the orally administered ethyl ester of L-α-methyldopa (250 mg.–750 mg.) was dose dependent while that of L-α-methyldopa (250 mg.–750 mg.) was not and (2) the peak plasma level of L-α-methyldopa was achieved more uniformly and rapidly for the L-α-methyldopa ester (45–60 minutes) than for the L-α-methyldopa (60–300 minutes). The absorption characteristics were determined by measuring plasma and urine levels of L-α-methyldopa. The average % absorption and the peak time were recorded. The data thus obtained is presented in the following table.

Table I

| | 250 mg. Dose | | 500 mg. Dose | | 750 mg. Dose | |
|---|---|---|---|---|---|---|
| Compound | Avg. % Abs. | Peak Time | Avg. % Abs. | Peak Time | Avg. % Abs. | Peak Time |
| L-α-methyl-dopa | 25 | 1–5 hr.* | 25 | 1–5 hr. | 25 | 1–5 hr.* |
| L-α- | | | | | | |

Table I-continued

| | 250 mg. Dose | | 500 mg. Dose | | 750 mg. Dose | |
|---|---|---|---|---|---|---|
| Compound | Avg. % Abs. | Peak Time | Avg. % Abs. | Peak Time | Avg. % Abs. | Peak Time |
| methyl-dopa ethyl ester | 10.8 | 45–60 min. | — | | 21 | 45–60 min. |

*Variable

With increasing dosages of the ethyl ester of L-α-methyldopa, the fraction of dose which is absorbed into the systemic circulation as L-α-methyldopa also increases. The effect of dose of orally administered ethyl esters on the urinary excretions of L-α-methyldopa in the dog is shown in the following table:

Table II

| Dose (mg./kg.) | % of dose excreted as L-a-methyldopa |
|---|---|
| 7.5 | 12.3 |
| 15.0 | 17.2 |
| 30.0 | 21.9 |
| 60.0 | 30.1 |
| 120.0 | 39.8 |

Since the antihypertensive effect of L-α-methyldopa appears to be related to the amount of L-α-methyldopa in the systemic circulation (Saavedra et al. Eroup. J. Clin. Pharmacol. 8, 381 (1975), the dosages of 250 mg.–500 mg. of L-α-methyldopa will be more antihypertensive effective than equivalent dosages of L-α-methyldopa ethyl ester. However, at individual dosages of over 500 mg., the percentage of L-α-methyldopa ethyl ester absorbed is equal to or greater than for the same dosage of L-α-methyldopa - and thus, the antihypertensive effect on oral administration of single doses of over 500 mg. of said ester will be greater than that for L-α-methyldopa. In addition, since the time to peak L-α-methyldopa plasma level occurs substantially sooner for said ester than for the L-α-methyldopa, the L-α-methyldopa ethyl ester will cause a more rapid reduction in high blood pressure (hypertension) than L-α-methyldopa, orally administered.

The present treatment (and formulations) clearly offer an unexpected advantage to hypertensive humans who require single L-α-methyldopa doses of more than 500 mg. Furthermore, where the required daily dosage exceeds 500 mg. for a hypertensive patient, using the present treatment method composition the number of individual doses and total daily dose required to provide effective control of hypertension may be reduced. For example, if a patient's daily dose of α-methyldopa is 1500 mg. taken in four individual doses at 375 mg. per dose (375 g.i.d.), then by using the L-α-methyldopa ethyl ester, a single dose of 1500 mg. or less per day will be sufficient.

Claims to the invention follow.

What is claimed is:

1. A method of treating hypertension which comprises oral administration in non-liquid form once daily to a hypertensive human of about 750 mg. to about 2500 mg. of the ethyl ester of L-α-methyl-3,4-dihydroxyphenylalanine, or a pharmaceutically acceptable salt thereof.

2. The method of claim 1 wherein said dose is about 750 mg.

3. The method of claim 1 wherein said dose is about 1000 mg.

4. The method of claim 1 wherein said dose is about 1500 mg.

5. The method of claim 1 wherein said dose is about 2000 mg.

6. The method of claim 1 wherein said dose is administered in a single dosage unit.

7. A pharmaceutical composition in a unit dosage non-liquid form of a capsule or tablet for oral administration to a hypertensive human comprising about 750 mg. to about 2500 mg. of L-α-methyl-3,4-dihydroxyphenylalanine or a pharmaceutically acceptable salt thereof, and pharmaceutically acceptable compounding ingredient.

8. The composition of claim 7 wherein said dosage form contains about 2000 mg. of said ester or salt thereof.

9. The composition of claim 7 wherein said dosage form contains about 750 mg. of said ester or salt thereof.

10. The composition of claim 7 wherein said dosage form contains about 1000 mg. of said ester or salt thereof.

11. The composition of claim 7 wherein said dosage form contains about 1500 mg. of said ester or salt thereof.

12. The composition of claim 6 wherein said dosage form contains about 2000 mg. of said ester or salt thereof.

13. The composition of claim 6 wherein said dosage form contains about 2500 mg. of said ester or salt thereof.

* * * * *